United States Patent

Servas et al.

[11] 3,939,078
[45] Feb. 17, 1976

[54] EXTRACORPOREAL FILTER

[75] Inventors: Francis Martin Servas, Belle Mead, N.J.; Jorge Torres, Newbury Park, Calif.

[73] Assignees: Johnson & Johnson, New Brunswick, N.J.; Purolator, Inc., Del.

[22] Filed: Apr. 19, 1974

[21] Appl. No.: 462,452

[52] U.S. Cl. ............... 210/436; 210/472; 210/539; 210/DIG. 23
[51] Int. Cl.² ........................................ B01D 35/00
[58] Field of Search............ 210/436, DIG. 23, 472, 210/539

[56] References Cited
UNITED STATES PATENTS
3,701,433   10/1972   Krakauer et al. .................. 210/436

Primary Examiner—Charles N. Hart
Assistant Examiner—Richard W. Burks

[57] ABSTRACT

An extracorporeal filter having improved characteristics for the positive elimination of gas bubbles from blood streams. The top of the filter housing is sloped to a high point where there is positioned an air vent. The inlet for the blood is positioned substantially in the center of the top portion and extends past the plane of the top portion into the filter housing.

2 Claims, 2 Drawing Figures

U.S. Patent  Feb. 17, 1976  3,939,078
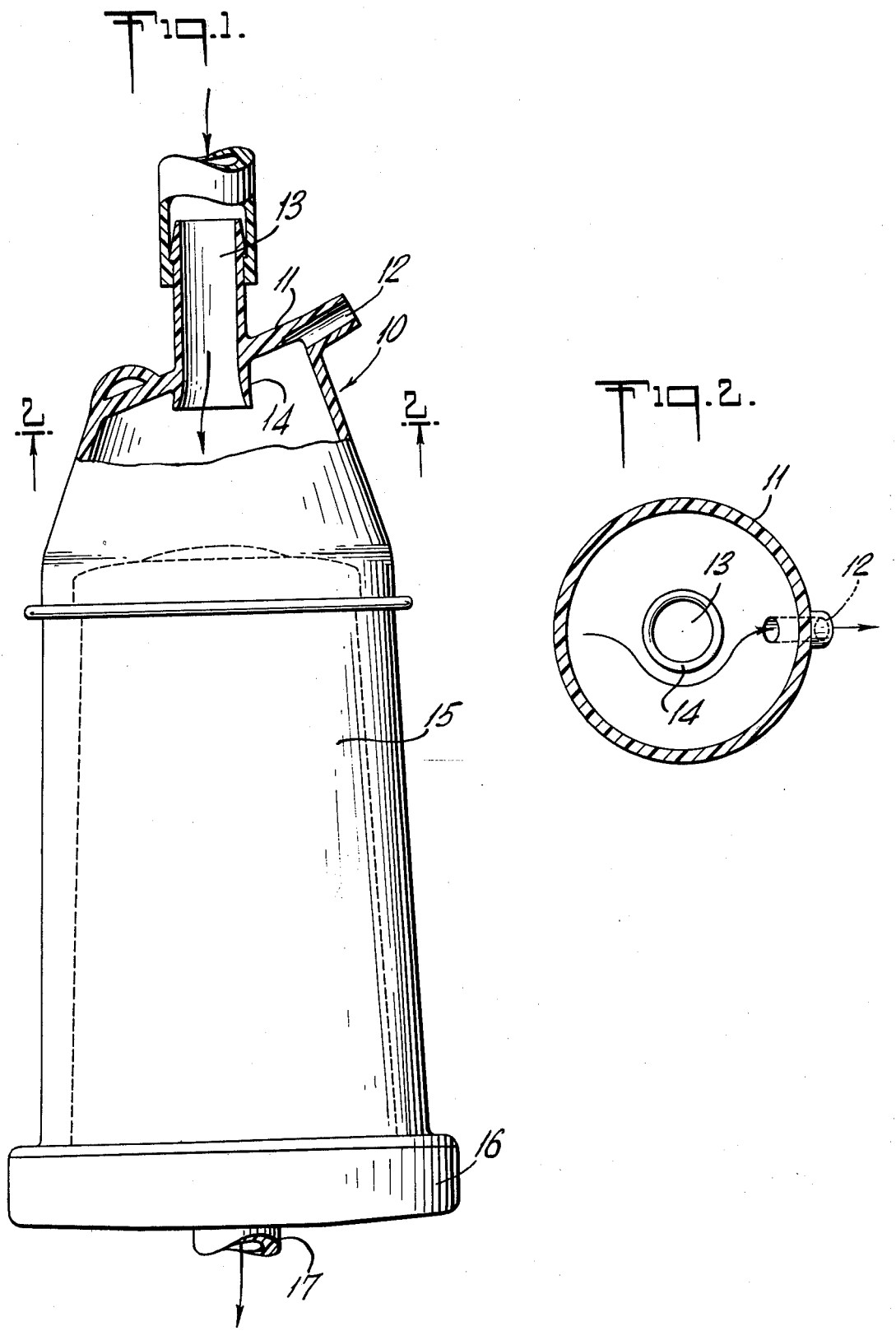

EXTRACORPOREAL FILTER

A new and improved blood filter for use in extracorporeal blood circulation.

BACKGROUND OF THE INVENTION

With new and improved surgical techniques developed over recent years in operations involving the heart, lungs and chest of the patient there has been increased usage of what is known as the heart-lung machine. With many of these new surgical techniques the length of time during which a heart-lung machine is used is also increasing. In simple terms the heart-lung machine comprises a pump for the blood and an oxygenator for placing oxygen and releasing carbon dioxide from the blood. The blood which is circulated in such a machine is that of the patient and in some instances transfused blood may also be added. In the cardiopulmonary bypasss line there is placed a filter to remove undesirable material from the blood before the blood is returned to the patient. The filter not only removes undesirable materials which are present in the blood but is also used as a means to remove entrapped gas or air bubbles that are present in the blood.

We have discovered a new filter assembly which does an excellent and positive job of removing microbubbles of gas from the bloodstream. Also our new improved filter assembly unexpectedly reduces the harmful effects which filtration and degasification may have on blood.

SUMMARY OF THE PRESENT INVENTION

In accordance with the present invention our new filter assembly has an inlet for blood positioned at the top of the filter assembly. The blood outlet is positioned at the bottom of the filter assembly. Blood entering from the top of the assembly passes downwardly inside the assembly through a filter media and out the bottom of the assembly. The top of the assembly is sloped and at the uppermost point at the top of the assembly is a gas vent to allow the gas to be evacuated from the assembly and allow any gas removed from the blood as it passes through the assembly to escape. The inlet for the blood extends below the top sloped surface of the assembly a distance sufficient to bring the blood into the assembly without interference from the gas bubbles being removed from the blood as they are passing along the sloped top surface of the assembly to the gas vent.

DESCRIPTION OF THE DRAWINGS

The invention will be further described in conjunction with the accompanying drawings wherein:

FIG. 1 is a cross-sectional view of a filter assembly of the present invention, and FIG. 2 is a cross-sectional view taken along line 2—2 of FIG. 1.

DETAILED DESCRIPTION OF THE DRAWINGS

Referring to the drawings there is shown a filter assembly 10 of the present invention. The assembly has a sloping top surface 11. At the uppermost point of the sloping top portion there is a gas vent 12 to allow air and other gases to escape from the filter. Substantially in the center of the sloping top surface is the inlet 13 for the blood. A critical part of the present invention is that the inlet extends below the sloping top portion as seen at 14. In the body of the assembly there is placed filter media 15 in suitable configuraton for filtering the blood. The top of the media is capped and sealed and the bottom of the media is sealed into the bottom portion 16 of the filter. In the center of the bottom portion is the blood outlet 17. The blood enters through the center top inlet 13, moves down along the side walls of the assembly, through the filter media 15 and out the bottom outlet 17.

The filter assembly is placed in the line from the oxygenator to the patient. The blood after oxygenation contains excess gas which must be removed before the blood is returned to the patient. The gas is allowed to escape from the body of the filter by passing upwardly to the sloped top surface. The gas passes along the sloped top surface 11 to the uppermost point and out the gas vent 12 as indicated by the arrow in FIG. 2. The gas as it passes along the sloped top portion of our filter assembly is directed away from the incoming bloodstream in the inlet 13 by the shoulder 14 around the center inlet. The escaping gas is not reentrapped by the incoming blood. The elimination of the reentrapment of gas is the reason why our new filter assembly has reduced the deleterious effects that filtration and handling may have on blood.

The filter housing may be made from material which is inert to blood and which can be sterilized by steam sterilization, gas sterilization or radiation sterilization. We have found that suitable materials for the housing assembly are the polyolefins, such as polypropylene and polyethylene, the polycarbonates and various butadienestyrene resins.

It it preferred that the filter assembly be tapered from inlet to outlet as shown in FIG. 1. This shape aids in forcing gas in the assembly upwardly to the surface. It is desirable to have edges relatively smooth and rounded especially at the collar 14 around the inlet to aid in the smooth flow of blood and cause the least turbulence in these flows. The size of the inlet and outlet may vary; quarter inch diameter and three-eights inch diameter inlets and outlets have been found suitable.

The gas vent may incorporate any of the standard connectors or valves such as a stop cock, luer adaptor, built-in ball valve and the like.

The filter media may be any of the standard sieve type or depth type filter medias such as woven polyester fabric or woven nylon filter fabric or the nonwoven fabrics and felts or the foam materials. The specific media will be dependent on where the filter is to be used and the type of solid or liquid particles to be removed from the blood.

Having now described the present invention in its preferred embodiment what we claim as new is:

1. An extracorporeal blood filter having improved characteristics for removing excess gas from the blood being filtered comprising a filter media mounted in a housing; said housing having a straight, smooth, uniformly sloped top surface from a low point positioned at the circumference of said housing to a high point positioned at the circumference of said housing directly opposite said low point, an inlet for the blood positioned in the top surface, a gas vent positioned at said high point, said blood inlet having a portion extending below the sloped top surface into the housing, said portion being free and open and not in contact with any other part of said filter whereby gas escaping to the vent is directed away from the entering bloodstream.

2. An extracorporeal blood filter according to claim 1 wherein the blood inlet is positioned substantially in the center of the sloping top surface.

* * * * *

UNITED STATES PATENT AND TRADEMARK OFFICE
CERTIFICATE OF CORRECTION

PATENT NO. : 3,939,078

DATED : February 17, 1976

INVENTOR(S) : Servas, Francis Martin
Torres, Jorge

It is certified that error appears in the above-identified patent and that said Letters Patent are hereby corrected as shown below:

In Column 2, Line 48, the word "woven nylon filter fabric" should read --- "woven nylon fabric" ---.

Signed and Sealed this fifteenth Day of June 1976

[SEAL]

Attest:

RUTH C. MASON
*Attesting Officer*

C. MARSHALL DANN
*Commissioner of Patents and Trademarks*